(12) United States Patent
Prasad

(10) Patent No.: US 7,256,389 B2
(45) Date of Patent: Aug. 14, 2007

(54) GLASS BOTTLE INSPECTION MACHINE

(75) Inventor: Mukesh Prasad, Windsor, CT (US)

(73) Assignee: Emhart Glass SA, Cham (CH)

(*) Notice: Subject to any disclaimer, the term of this patent is extended or adjusted under 35 U.S.C. 154(b) by 0 days.

(21) Appl. No.: 11/269,482

(22) Filed: Nov. 7, 2005

(65) Prior Publication Data

US 2007/0102628 A1 May 10, 2007

(51) Int. Cl.
- *B07C 5/12* (2006.01)
- *G01N 21/86* (2006.01)
- *G01N 21/00* (2006.01)
- *G01N 21/90* (2006.01)
- *G06K 9/00* (2006.01)

(52) U.S. Cl. .............. 250/223 B; 250/559.44; 356/239.4; 356/427; 382/142

(58) Field of Classification Search ........ 382/142; 356/237.1, 239.4, 239.5, 239.6, 240.1, 427, 356/428; 250/223 B, 559.44, 559.45, 559.47, 250/559.48
See application file for complete search history.

(56) References Cited

U.S. PATENT DOCUMENTS 5,557,869 A * 9/1996 Douglas et al. ............. 382/12

* cited by examiner

*Primary Examiner*—Georgia Epps
*Assistant Examiner*—Don Williams
(74) *Attorney, Agent, or Firm*—Spencer T. Smith

(57) ABSTRACT

A camera based inspection system for inspecting glass bottles made in a glass-forming machine. A single picture shows the heat distribution of an inspected portion of the bottle over a period of time whereby the operator will see a loss of stability in the glass process.

5 Claims, 2 Drawing Sheets

GLASS BOTTLE INSPECTION MACHINE

The present invention relates to inspection machines, which inspect glass bottles made in a glass-forming machine such as an I.S. (individual section) machine.

BACKGROUND OF THE INVENTION

The process of making a glass bottle must be precisely controlled if the creation of bottle defects which would require the rejection and removal of formed bottles is to be minimized. In this process it is desirable to identify a defective bottle as quickly as possible and the ideal time is the time between the removal of a formed bottle from the machine and the time when the bottle enters the Lehr where it will be annealed. During this period of time the surface temperature of the glass bottle is very hot and camera based inspection systems are available that can record and evaluate the surface temperature of the bottle. Such systems also can present a color-coded representation of the heat pattern on the bottle surface.

OBJECTS OF THE INVENTION

It is an object of the present invention to provide a representation of the formed bottles that will provide valuable information to the plant.

Other objects and advantages of the present invention will become apparent from the following portion of this specification and from the accompanying drawings, which illustrate a presently preferred embodiment incorporating the principles of the invention.

BRIEF DESCRIPTION OF THE PREFERRED EMBODIMENT

Figure 2:
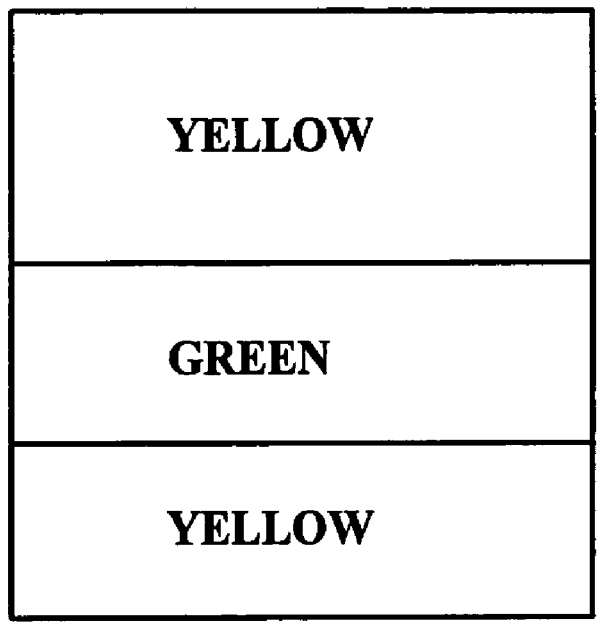
FIG. 2 is a view of the computer screen shown in FIG. 1, showing a stable process.
Figure 3:
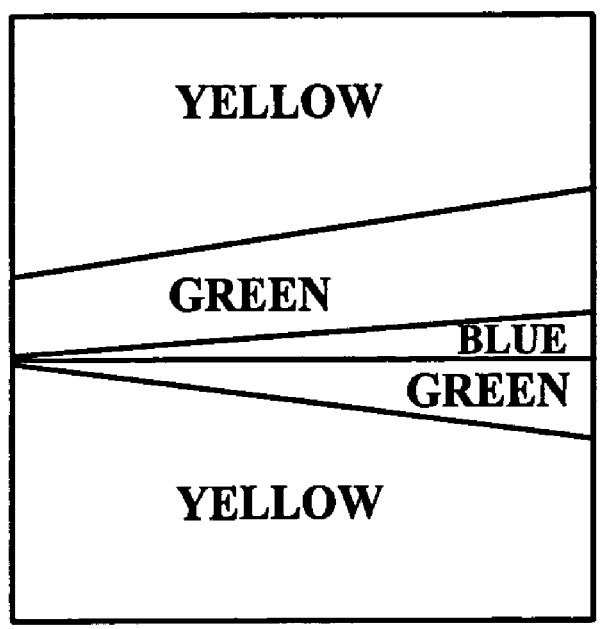
FIG. 3 is a view of the computer screen shown in FIG. 1, showing a process that has become unstable.

A bottle 10 formed in a glass forming machine is conveyed on a conveyor 12 from the machine to a Lehr. The bottle is viewed at an inspection station by a camera based inspection system 14 which includes a camera 16 which transmits an image of the bottle to a CCD storage device 18 The storage device stores the image 20 so that it can be evaluated. As shown, a plurality of data points A1,A2, B1,B2, C1,C2, etc. . . . , are selected at each of a plurality of vertical locations within an area of interest on the formed bottle. A vertical strip of data 20 is defined and stored representing that averaged data; $A_{ave.}$, $B_{ave.}$, $C_{ave.}$, for a particular bottle made in a particular mold of the machine (the bottle carries a mold number which will be read and assigned to each inspected bottle). The computer supplies the computer screen 22 with "N" ("N" can be selected by the operator) adjacent vertical data strips 20/1, 20/2 . . . , 20/N (the current data strip (20/N) and the last N−1 consecutive data strips), hereinafter referred to as a mold/time picture. FIGS. 2 and 3 shows a mold/time picture when the process is stable (FIG. 2) and a mold/time picture when the process has become unstable (FIG. 3). In fact, the computer screen, for bottles being made in a twelve section, quad gob machine could present 48 of these mold/time pictures, one for each of the 48 molds.

Figure 1:
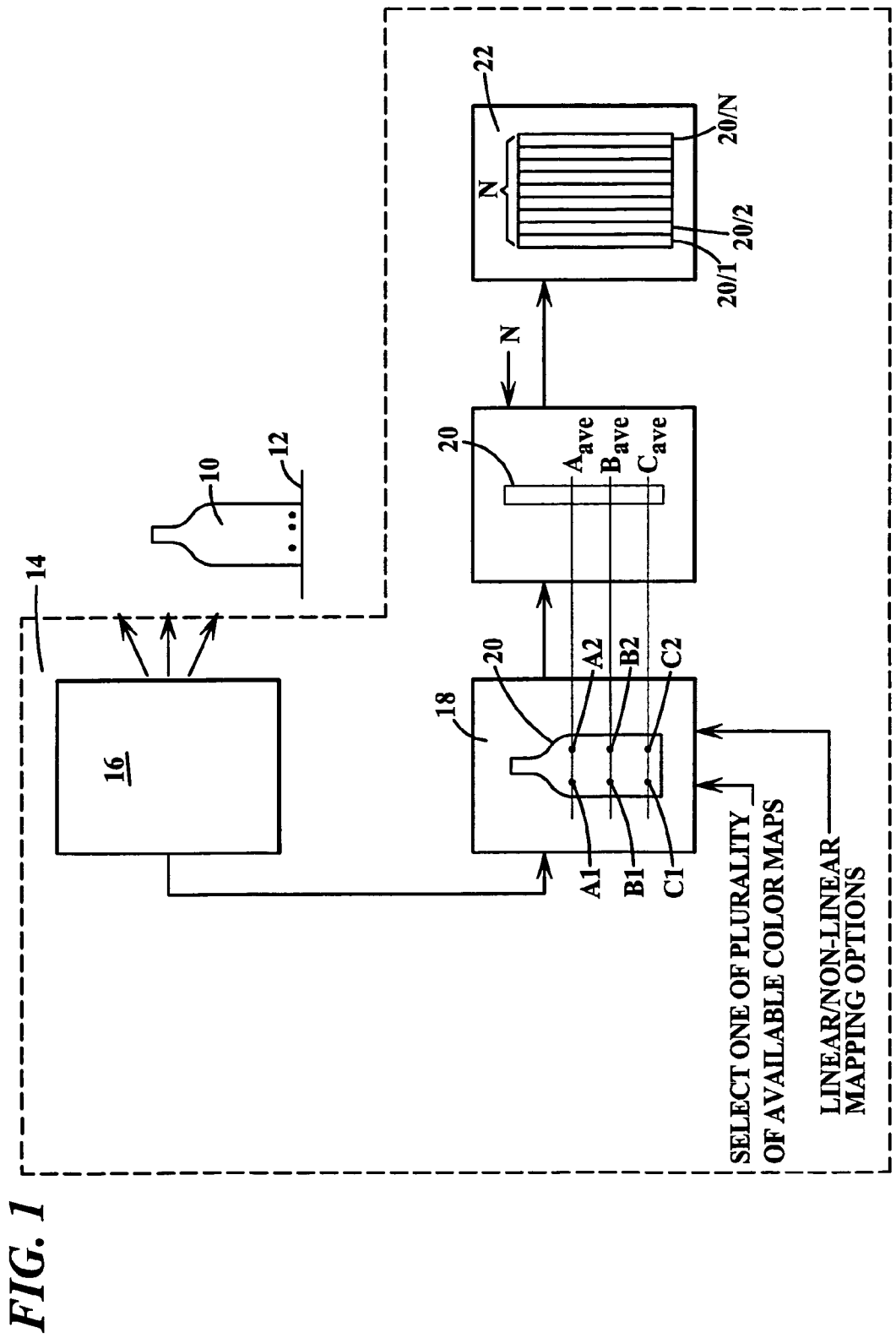
FIG. 1 is a schematic view of an inspection machine made in accordance with the teachings of the present invention.

As shown in FIG. 1, the operator can select one of a plurality of color maps and can rotate through these maps. Different color maps can help to highlight different types of problems, e.g., cold spots vs. hot spots at different locations, for example. The operator can also select from linear and non-linear (using a function such as y=x squared or y=x cubed) mapping options. Non-linear mapping can be used to examine particular areas in detail, e.g., areas that are close to 400 degrees F., for example.

What is claimed is:

1. A machine for inspecting glass bottles formed in a particular mold in a glass-forming machine comprising a camera system
   for viewing bottles at an inspection location,
   for presenting an image of an inspected bottle,
   for evaluating a portion of the image of the bottle and defining a vertical data strip representative of the portion of the image evaluated, and
   for presenting a mold/time picture of bottles including "N" chronologically related vertical data strips.

2. A machine for inspecting bottles formed in a particular mold in a glass-forming machine according to claim 1, wherein the glass machine is an I.S. machine.

3. A machine for inspecting bottles formed in a particular mold in a glass forming machine according to claim 1, wherein the vertical data strip is defined with a selected color map representing the temperature of the viewed glass.

4. A machine for inspecting bottles formed in a particular mold in a glass-forming machine according to claim 3, wherein there are a plurality of selectable color maps.

5. A machine for inspecting bottles formed in a particular mold in a glass-forming machine according to claim 1, wherein the operator can select from linear and non-linear mapping options.

* * * * *